United States Patent [19]

Wille

[11] Patent Number: 5,204,086
[45] Date of Patent: Apr. 20, 1993

[54] X-RAY CONTRAST AGENT

[75] Inventor: Knut Wille, Østerås, Norway

[73] Assignee: Nycomed Imaging AS, Oslo, Norway

[21] Appl. No.: 902,810

[22] Filed: Jun. 25, 1992

Related U.S. Application Data

[63] Continuation of Ser. No. 119,346, Nov. 10, 1987, abandoned, which is a continuation of Ser. No. 917,025, Oct. 9, 1986, abandoned, which is a continuation of Ser. No. 537,836, Sep. 30, 1983, abandoned.

[30] Foreign Application Priority Data

Oct. 1, 1982 [GB] United Kingdom .............. 8228067

[51] Int. Cl.$^5$ ............................................. C07C 237/46
[52] U.S. Cl. ......................................... 424/5; 564/153
[58] Field of Search ............................ 564/153; 424/5

[56] References Cited

U.S. PATENT DOCUMENTS

| | | | |
|---|---|---|---|
| 4,001,323 | 1/1977 | Felder et al. | 564/153 |
| 4,021,481 | 5/1977 | Almen et al. | 424/5 |
| 4,250,113 | 2/1981 | Nordal et al. | 564/153 |
| 4,328,202 | 5/1982 | Gries et al. | 424/5 |
| 4,348,377 | 9/1982 | Felder et al. | 564/153 |
| 4,352,788 | 10/1982 | Felder et al. | 564/153 |
| 4,364,921 | 12/1982 | Speck et al. | 564/153 |
| 4,547,357 | 10/1985 | Pfeiffer et al. | 564/153 |

FOREIGN PATENT DOCUMENTS 74309 3/1983 European Pat. Off. .............. 424/5

OTHER PUBLICATIONS

Weislander et al., *Acta Radiologica* (1987) Supplement, 370, pp. 73–77.
Halkala et al., *Investigative Radiology*, Sep. 1988, Suppl. 1, vol. 23, pp. 5200–5202.
Michelet, *Acta Radiologica*, 1987, 28, Fasc 3, pp. 329–333.
Almen, *Acta Radiologica* (1987) Supplement, 370, pp. 69–72.

Primary Examiner—Allen J. Robinson
Assistant Examiner—Scott C. Rand
Attorney, Agent, or Firm—Bacon & Thomas

[57] ABSTRACT

Compounds of the general formula:

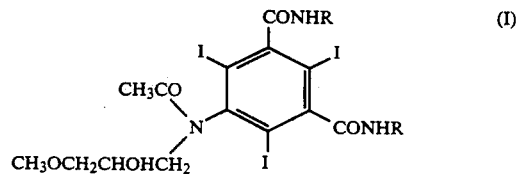

(wherein R represents —CH(CH$_2$OH)$_2$ or —CH$_2$CH(OH)CH$_2$OH) possess a package of favorable parameters which render them of particular use not only in all forms of intravascular visualization but also in myelography.

The compounds are prepared by reaction of the corresponding 5-monoacetylamino compound with one or more reagents effective to introduce the 2-hydroxy-3-methoxypropyl group.

8 Claims, No Drawings

X-RAY CONTRAST AGENT

This application is a continuation of application Ser. No. 07/119,346, filed Nov. 10, 1987, now abandoned, which is a continuation of application Ser. No. 06/917,025, filed Oct. 9, 1986, now abandoned, which is a continuation of application Ser. No. 06/537,836, filed Sep. 30, 1983, now abandoned.

This invention relates to novel non-ionic iodinated X-ray contrast agents for myelographic and vascular use.

In our British Patent Specification No. 1,321,591 we describe and claim certain non-ionic compounds as X-ray contrast agents, such compounds representing an important advance over previously known ionic X-ray contrast agents in respect of side effects due to high concentrations of ions and/or to high osmolality. Such compounds are suitable for one or more possible fields of X-ray visualisation but are not usually suitable for a wide range or spectrum of such uses. In general, non-ionic X-ray contrast agents may be of use in two main fields, namely:

Intravascular visualisation, including urography and angiography, for example cerebral, coronary and peripheral angiography, and Myelography, i.e. injection into the cerebrospinal fluid.

Radiologists have used different X-ray contrast agents particularly adapted to different fields of use but there are clearly advantages if it is possible to use a single X-ray contrast agent for a wide range of uses; apart from economies of scale in manufacture, it is also more satisfactory for the radiologist to be able to use experience of a contrast agent gained in one field of use, e.g. urography, in some other field, e.g. angiography or myelography. For the purposes of this specification an X-ray contrast agent which can be used in all forms of intravascular visualisation and myelography is termed a 'general X-ray contrast agent'.

In our British Patent No. 1,548,594 we describe and claim two specific compounds which may be used as 'general X-ray contrast agents' and which fulfil a 'package' of favourable parameters namely low toxicity, low osmolality, high stability, ease of manufacture and the ability to produce solutions of high concentration but low osmolality. Low viscosity at high concentrations is also desirable. As stated in British Patent No. 1,548,594 whilst the minimum standard for each parameter is not necessarily exceptionally high in itself, it is very unusual to find a compound which possesses the whole 'package' of favourable properties at a suitably high level.

It is known that X-ray contrast agents which possess close structural similarities may nevertheless possess very different properties such as for example toxicity. Thus it is a difficult empirical task to identify a compound which possesses a complete package of favourable parameters and which can be used as a general X-ray contrast agent.

The present invention is based on the discovery of two isomeric N,N'-bis(dihydroxypropyl)-5-[N-(2-hydroxy-3-methoxypropyl)acetamido]-2,4,6-triiodoisophthalamides of the formula:

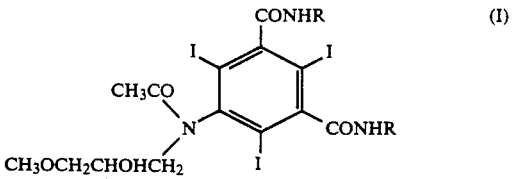

(where R represents —CH(CH$_2$OH)$_2$ or —CH$_2$CH(OH)CH$_2$OH) which fulfil the above mentioned parameters of low toxicity, low osmolality, high stability and ease of manufacture as set out in British Patent No. 1,548,594, whilst in addition possessing high solubility and more particularly a zero or very low crystal growth rate. These factors ensure that the compounds of the invention can be used as general X-ray contrast agents whilst ensuring the high stability of even their supersaturated solutions. The zero or very low crystal growth rate of the compounds of formula I enables highly concentrated solutions of the compounds to be stored for long periods without the risk of crystalline material separating out of solution. It is clearly advantageous to formulate X-ray contrast agents in sterile solutions rather than for the radiologist to have to prepare a sterile solution immediately prior to use from the X-ray contrast agent in freeze-dried form. Such solutions prepared by the radiologist cannot be stored for any length of time and as a result X-ray contrast agent is wasted through the need to dispose of unused solution. On the other hand where X-ray contrast agents are formulated as sterile solutions it is advantageous for the agent to have as low a crystal growth rate as possible in order to mitigate the risk of crystalline material separating out of solution.

Thus according to the present invention we provide the compounds of formula I as hereinbefore defined including the stereoisomeric forms thereof separately or in combination. These compounds are not specifically disclosed in our British Patent Specification No. 1,321,591, and represent a substantial and valuable advance over the compounds generally disclosed in our above British Patent Specification.

The compound of formula I in which R is —CH(CH$_2$OH)$_2$, namely N,N'-bis(1,3-dihydroxy-2-propyl)-5-[N-(2-hydroxy-3-methoxypropyl)acetamido]-2,4,6-triiodoisophthalamide (compound A), exists in the form of both exo- and endo-isomers and both such isomers are included within the scope of the present invention. Moreover the compound contains a chiral carbon atom and thus exists in optically active forms. The present invention thus includes the d-, l- and racemic forms of the compound of formula I in which R is —CH(CH$_2$OH)$_2$.

The compound of formula 1 in which R is —CH$_2$CH(OH)—CH$_2$OH namely N,N'-bis (2,3-dihydroxypropyl)- 5-(N-2-hydroxy-3-methoxypropyl)acetamido-2,4,6-triiodoisophthal-amide (Compound B) also exists in the form of endo and exo isomers, but in addition to the chiral centre in the 3-methoxy-2-hydroxypropyl chain, also possesses chiral centres in the two groups R. Since rotation about the bond between the nitrogen atom and the benzene nucleus is, in addition, strongly restricted, there are eight enantiomers forming four racemates and the invention extends to all the above isomeric forms.

Compound A has been found to possess an intravenous toxicity (LD$_{50}$i.v) in the mouse of >18,000 mg I/kg while that of Compound B is 22,000; the maximum intravenous toxicity limit proposed in British Patent No. 1,548,594 as suitable for a general X-ray contrast agent is 17,000 mg I/kg.

The intracerebral toxicity ($LD_{50}$ i.c.) in the mouse of Compound A is 1850 mg I/kg, while that of Compound B is greater than 1750 mg I/kg; the maximum intracerebral toxicity limit proposed in British Patent No. 1,548,594 as suitable for a general X-ray contrast agent being 1500 mg I/kg.

The nephrotoxicity in the rabbit of both Compound A and Compound B is greater than 10,500 mg I/kg this being the nephrotoxicity limit proposed in British Patent No. 1,548,594 as suitable for a general X-ray contrast agent; Compound A possesses low osmolality: 0.75 at 300 mg I/ml, this being the maximum osmolality limit proposed in British Patent No. 1, 548,594 as suitable for a general X-ray contrast agent, whilst Compound B possesses an osmolality of 0.66 at 300 mg I/ml. Compound A possesses a viscosity of 6.1 cP at 37° and 12.7 at 20° C., the concentration being 300 mg I/ml in each case. The maximum viscosity proposed in British Patent No. 1,548,594 for suitability as a general X-ray contrast agent is 6.5 cP at 37° C. (concentration 300 mg I/ml).

Compound A possesses a relatively high solubility in water, namely 31 g/100 ml (141 mg I/ml) at 20° C. and 38 g/100ml (173 mg I/ml) at 37° C. At relatively high concentrations the majority of known non-ionic X-ray contrast agents probably exist as supersaturated solutions rather than as true aqueous solutions. The above solubility characteristics enable the compounds of the invention to be used at concentrations of about 40 g/100ml without supersaturation at body temperature.

Compound B forms highly concentrated solutions, for example, 100 g/100 ml without any tendency to crystallise. This may well be due to the number of isomeric species present. It will be appreciated that a supersaturated solution is thermodynamically unstable and is liable to crystallise unexpectedly, particularly if contacted with seed crystals. Such crystallisation could lead to the injection of significant quantities of crystalline material so causing tissue damage. Such damage would depend in part on the size of the crystals which were inadvertently injected and clearly microfine crystals would not give rise to this problem; suspensions of microfine crystals are, in fact, frequently formulated for injection.

We have found that supersaturated solutions of Compound A crystallise, even when seeded, extremely slowly. One advantage of this is that the tendency to crystallise from supersaturated solution is greatly reduced, so that such solutions can be stored for long periods. Naturally, using modern pharmaceutical techniques it is possible to minimise any possibility of seed crystals being present. However, even if crystallisation does begin, the very slow rate of crystallisation as well as the relatively high solubility at body temperature mean that the crystals remain very small in the vials and dissolve rapidly in the body fluid if injected.

The compounds of the present invention are thus of particular interest as general X-ray contrast agents in that their supersaturated solutions may be stored for long periods without risk of formation of crystals which could cause tissue damage on injection. The very low crystal growth rate of Compound A makes the true solubility of the compound less critical. These properties of the compounds of formula I in particular render them an important and valuable advance over many X-ray contrast agents generally disclosed in the literature including our above-mentioned Patent Specifications.

With regard to stability, the compounds of formula I have been found to be stable to autoclaving at 120° C. for 20 minutes. In this connection it should be noted that the compounds of formula I contain a m-carboxamido-o-iodo-N-($\beta$-hydroxyalkyl) aniline moiety which tends to lead to intramolecular cyclisation with displacement of iodine, as described in our British Patent 2,031,405. For this reason the compounds of formula I are preferably autoclaved for sterilisation in the presence of a physiologically acceptable buffer system the pH of which decreases with increasing temperature, for example ammonia or an amine having a pKa at 15° C. of less than or equal to 9.5, as described in our above British Patent Application. We have found that autoclaving of a 300 mg I/ml solution of Compound A containing 10 mM TRIS and 0.32 mg per gram of $CaNa_2$ EDTA at 120° C. for 20 minutes resulted in a pH drop of only 0.06 pH units from pH 7.35 to 7.29 and an increase in inorganic iodide of from 11 g/ml to only 17 g/ml. No change was observed by TLC and HPLC.

As indicated in British Patent No. 1,548,594 referred to above, one important element of the package of favourable parameters necessary for a successful X-ray contrast agent is ease of manufacture. Such products are used in relatively large quantities and it is important that they can be produced cheaply. The most important compound of the above patent is iohexol, which is the desmethyl analogue of Compound B according to the present invention, that is it carries on the 5-acetamido nitrogen atom the group $HOCH_2CHOHCH_2$—instead of $CH_3OCH_2CHOHCH_2$—. The final stage in the production of both Compound B and iohexol is normally the introduction of the above groups into the intermediate N,N'-bis(2,3-dihydroxypropyl)-5-acetamido-2,4,6-triiodoisophthalamide by an 'alkylation' reaction. In both cases, there is inevitably some alkylation of the hydroxyl groups already present in the above intermediate and it is necessary to separate out such overalkylated products.

We have found that in the case of iohexol, the introduction of additional 2,3-dihydroxypropyl groups greatly increases the hydrophilicity of the overalkylated by-products and it is difficult to remove these from the highly hydrophilic iohexol. Thus, the most effective method of purification of iohexol is crystallisation from boiling isopropanol at a concentration of 0.2 kg/liter but it is found that only 25–30% of the overalkylated by-products can be removed in a sin9le crystallisation of this type. Further crystallisation steps significantly increase the cost of the process. In contrast, in the case of Compound B, overalkylation introduces one or more 3-methoxy-2-hydroxypropyl groups and increases the hydrophobic character of the molecule. In this case, a single crystallisation from isobutanol at a concentration of 0.2 kg/liter removes up to 85% of the overalkylated products, thus leading to considerable savings in time, solvents and plant costs.

The compounds of the present invention thus both possess the above-mentioned 'package' of favourable parameters including ease of manufacture and are therefore of particular interest as general X-ray contrast agents.

The present invention also provides radiological compositions comprising as active ingredient at least one of the compounds of formula I as hereinbefore defined in association with an inert carrier.

The radiological compositions of the present invention are conveniently presented in a form suitable for administration by injection, for example, in ampoules or vials. The capacity of the ampoule or vial may be, for example, from 5 to 500 ml and the concentration may, for example, be from 20 to 500 mg I/ml.

The compounds of the present invention may be prepared in any convenient manner, but the following process is of particular interest and constitutes a further feature of the present invention.

Thus there is provided a process for the preparation of the compounds of formula I as hereinbefore defined which comprises reacting the compound of formula:

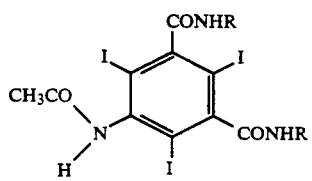

(where R has the above meanings) or a derivative thereof having one or more protecting groups such as acyl groups, e.g. acetyl, or cyclic acetals or ketals, with one or more reagents effective to introduce the 2-hydroxy-3-methoxypropyl group for example, a compound of the formula:

CH₃OCH₂CHOHCH₂X     (III)

(wherein X represents an atom or group removable as an anion) or a derivative thereof having a protecting group e.g. an acyl group, followed, where necessary, by hydrolysis of any unwanted protecting groups whereby a compound of formula I as hereinbefore defined is obtained.

Where a compound of formula III is used, this is preferably a reactive ester derivative such as a compound of formula III in which X represents a halogen atom e.g. a chlorine or bromine atom, or a sulphate or hydrocarbon-sulphate group e.g. a tosyl or mesyl group. The reactive derivative is preferably reacted with the acetamido starting material under basic conditions, for example in a non-aqueous medium, e.g. in an alkanol such as methanol, ethanol, 2-methoxyethanol, and/or propylene glycol. Propylene glycol may for example be used in admixture with methanol and/or ethanol. A base, conveniently an alkali metal alkoxide such as sodium methoxide, or an alkali metal hydroxide such as sodium or potassium hydroxide is preferably used. It is also possible to react the acetamido compound with an epoxide, i.e. methoxymethyloxirane.

Thus, for example, a compound of formula I may be prepared by reaction of a compound of formula II with 2-hydroxy-3-methoxypropyl chloride preferably in the presence of propylene glycol and/or methanol with, for example, sodium hydroxide as base.

As indicated above, it is normally necessary to remove over-alkylated by-products, for example by crystallisation.

The compounds of formula II may be prepared in any convenient manner, for example, by reaction of 5-acetamido-2,4,6-triiodoisophthaloyl chloride and/or 5-diacetylamino-2,4,6-triiodoisophthaloyl chloride with 1,3-dihydroxy-2-propylamine or 2,3-dihydroxypropylamine followed, where the 5-diacetyl amino compound is used by removal of one N-acetyl group, e.g. by alkaline hydrolysis at slightly elevated temperature. The reaction may, for example, be effected in the presence of dimethylformamide or dioxan as solvent, conveniently in the additional presence of an alkali metal or alkaline earth metal carbonate or bicarbonate such as potassium bicarbonate.

A compound of formula II may also be prepared for example, by acetylation of a compound of the formula:

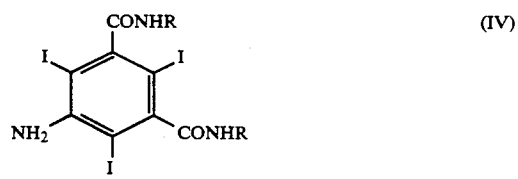

(where R has the above meanings)

Acetylation may be effected by any convenient method e.g. by the use of acetic anhydride (which can also serve as the solvent) together with catalytic amounts of a mineral acid e.g. sulphuric or perchloric acid, or by the use of an acid halide preferably in a polar solvent such as dimethylformamide or dimethylacetamide. Where unwanted O-acetyl groupings are formed or other protecting groups are present these may be removed either at this stage or after the hydroxyalkylation of the O-acetylated or protected compound. The basic hydrolysis of the O-acetyl grouping may for example, be effected using aqueous alkali metal hydroxide e.g. sodium hydroxide, the reaction preferably being carried out at slightly elevated temperature, e.g. about 50° C.

In addition, depending on the acetylating agent used, other products may be formed and require separation. When acetic anhydride is used with concentrated sulphuric acid as catalyst, the primary amino group is often, in part, bis-acetylated, such that an overacetylated product is obtained. In general a mixture of acetylated products will be obtained. If desired, the bis-acetylamino group may be hydrolysed to the monoacetylamino group under mild basic conditions e.g. by the use of sodium hydroxide in, for example, methanol prior to N-hydroxyalkylation. It is, however, possible to effect N-hydroxyalkylation using the bis-acetylamino compound with simultaneous solvolysis.

The compounds of the present invention are subject to endo/exo isomerism as is explained below. Referring to the following formula:

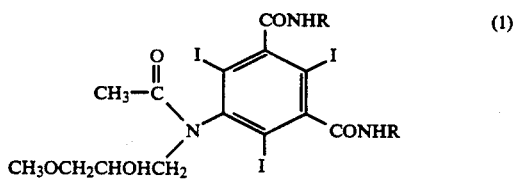

(where R has the above meanings) it will be appreciated that exo- and endo isomers exist due to restricted rotation of the N-CO bond (1) caused by steric hindrance from the adjacent bulky iodine atoms and the presence of the 2-hydroxy-3-methoxypropyl group bonded to the said N-atom. These isomers tend to equilibrate in solution but are sufficiently stable to be separated by thin layer chromatography.

The compounds of the present invention also exist in racemic and optically active forms, as explained above.

It will be appreciated that the individual optically active isomers of the compound of the invention can readily be obtained by conventional methods. Thus, for example, the individual optically active isomers of Compound A may be obtained by using an optically active 2-hydroxy-3-methoxypropylating agent to introduce the 2-hydroxy-3-methoxypropyl group. Separate optical isomers of the compounds of formula I can, if required, be mixed in equal proportions to produce a racemate. Similarly, Compound B can be prepared also using optically active side-chain intermediates.

The compounds of formula II as hereinbefore defined are important intermediates in the preparation of the compounds of formula I and constitutes a further feature of the present invention.

The preparation of the compounds of formula I and II are illustrated in the following in which temperatures are quoted in ° C. Radiological compositions containing the compounds of formula I of the present invention as active ingredient are also exemplified hereinafter:

PREPARATION

5-Acetamido N,N'-bis(1,3-dihydroxy-2-propyl)-2,4,6-triiodoisophthalamide

5-Amino-N,N'-bis(1,3-dihydroxy-2-propyl)-2,4,6-triiodoisophthalamide (300 g) was suspended in acetic anhydride (1.5 l) at 90° (in an oil bath) and then p-toluenesulphonic acid (3 g) was added. The mixture was heated for 4½ hours and then cooled slowly to room temperature. The product was collected on a filter and washed with small amounts of acetic anhydride. Yield: 353 g. The product was suspended in a mixture of methanol (600 ml) and water (300 ml) at room temperature and the pH was adjusted to about 11.5 by adding 5N sodium hydroxide (200 ml). This mixture was heated at 50° C. and more 5 N sodium hydroxide (235 ml) was added dropwise in such a manner that the pH was kept at about 10.5. After 2-3 hours the pH did not decrease, and the hydrolysis was completed. After cooling to room temperature the mixture was acidified with 6 N hydrochloric acid to about pH 6. After stirring for two hours at room temperature, the mixture was cooled to 3° for 2-3 days. The product was collected on a filter, suspended in water (500 ml) and filtered again. Yield: 257 g. Melting point: above 270°. (Found: C 25.68; H 2.85; I 51.0; N 6.03. Calc. for $C_{16}H_{20}I_3N_3O_7$: C 25.72;H 2.70; I 50.96; N 5.62) TLC (precoated TLC Plates Silica Gel 60 F-254 from Merck A.G. and developed in CHCl$_3$: MeOH=70:30) showed one spot with $R_f$ value 0.38.

EXAMPLE 1

N,N'-Bis(1,3-dihydroxy-2-propyl)-5-[N-(2-hydroxy-3-methoxypropyl)acetamido]-2,4,6-triiodoisophthalamide (Compound A)

5-Acetamido-N,N'-bis(1,3-dihydroxy-2-propyl)-2,4,6-triiodoisophthalamide (1036 g, 1.39 mol) was slurried in a mixture of propylene glycol (4170 ml) and methanol (4170 ml). After adding 18.25 M sodium hydroxide (114 ml, 2.08 mol), the mixture was heated at about 50°. When all or nearly all of the starting material was dissolved, the excess of methanol was evaporated in vacuo. Thereafter 2-hydroxy-3-methoxypropyl chloride (259 g, 2.08 mol) was added. The reaction mixture was heated at 50° for 44 hours and then stored at room temperature for 44 hours. Ater neutralization with concentrated hydrochloric acid, the reaction mixture was evaporated in vacuo. The residue was dissolved in methanol (3500 ml) and treated with a mixture of Dowex anion exchange resin 1×4 (2.87 kg) and Amberlite cation exchange resin (1.2 kg). The ion exchange resin was filtered off and washed with 80% aqueous methanol. The filtrate was evaporated in vacuo to dryness and the residue dissolved in isopropyl alcohol (5 l) at 80°. The product was precipitated by cooling to 13.5° and collected on a filter. Further purification was performed by recrystallization from isopropyl alcohol (4 l).

Yield: 577 g (Fraction I).

The two isopropyl alcohol mother liquors were collected and evaporated to dryness in vacuo. The temperature was increased from 60° to 105° to promote evaporation. The residue was recrystallized from isopropyl alcohol (2 l).

Yield: 419 g (Fraction II).

Fraction I and II were collected and dissolved in 80% aqueous methanol (2 l) at 55° and then the solution was evaporated to dryness in vacuo at 55°. Yield: 954 g. This procedure was performed to transfer the crystals in a more soluble form. The product was dissolved in methanol (1110 ml) and refluxed for 26 hours. Crystals, insoluble in hot methanol started crystallizing after about two hours. Additional amounts of methanol (250 ml) were added during the boiling. Then the mixture was cooled and stirred for 64 hours. 50 ml of methanol was added during the last step. The product was collected on a filter and washed with cold methanol. Yield 828 g. Then the product was dissolved in 80% aqueous methanol (2 l) at 55° and the solution evaporated to dryness in vacuo. The residue was dissolved in boiling methanol (1150 ml) and refluxed overnight. The mixture was diluted with more methanol (750 ml) during boiling. Crystals, insoluble in hot methanol, crystallized during this procedure. After cooling and stirring, the crystals were filtered off. Yield: 696 g. This product was dissolved in a mixture of methanol (1500 ml) and water (600 ml) and the solution evaporated to dryness in vacuo at 55°. Finally the residue was dissolved in water (700 ml) and evaporated to dryness in vacuo at 55°. Yield: 706 g. Melting point: 184°-186°. TLC (precoated TLC Plates Silica Gel 60 F-254 from Merck A.G. and developed in n-BuOH: HOAc: H$_2$O=50:11:25) showed two spots with R$_f$ values 0.45 and 0.53 in the ratio 1:4. The two spots represented the endo/exo isomers.

Analysis (Found: C 28.68; H 3.44; I 45.3; N 5.15; O 17.03. Calc. for $C_{20}H_{28}I_3O_9$: C 28.76; H 3.38; I 45.59; N 5.03; O 17.24).

EXAMPLE 2

N,N'-bis(2,3-dihydroxypropyl)-5-[N-(2-hydroxy-3-methoxypropyl)acetamido]-2,4,6-triiodoisophthalamide (Compound B)

To a suspension of 5-acetamido-N,N'-bis(2,3-dihydroxypropyl)-2,4,6-triiodoisophthalamide, prepared as in British Patent No. 1548594, (800 g, 1.07 mol) in propylene glycol (2.4 l) was added 16.5M sodium hydroxide (97.3 ml, 1.61 mol) and then the suspension was stirred at about 70° until the starting material was dissolved. Thereafter the solution was cooled to about 35° and 2-hydroxy-3-methoxypropyl chloride (199.8 g, 1.61 mol) was added. After about 16 h the reaction mixture was heated at about 50° for an additional 8 h. The reaction was quenched by adding hydrochloric acid and then the mixture evaporated in vacuo to dryness. The residue was suspended in methanol (2.3 1 and undissolved salts filtered off. The solution was diluted with water (575 ml) and treated with sufficient amounts of Amberlite$^R$ IR-120 cation exchange resin and Dowex$^R$ 1×4 anion exchange resin to remove inorganic salts. After filtration the solution was treated with charcoal and evaporated to dryness in vacuo. The residue was dissolved in 2-propanol (3.2 1) by heating and then the solution evaporated to dryness in vacuo. The residue was dissolved in hot 2-propanol (3.2 1) and the solution cooled to −40° whereby the product crystallized. The product was collected on a filter. Yield: 718 g. The crystals (700 g) was dissolved in boiling 2-propanol (2,8 1) and refluxed for 2 days. After some hours crystals insoluble in hot 2-propanol started to crystallize. The mixture was filtered while hot. Yield: 490 g. The crystals were dissolved in water and the solution evaporated to dryness in vacuo.

The product appeared as one spot with R$_f$ value 0.48 when it was applied to TLC (Silica gel 60-F254 from Merck A.G.) with elution with chloroform/methanol 70:30. The staring material had the R$_f$ value 0.39. The endo/exo isomers appeared as two spots with R$_f$ values 0.26 and 0.35 respectively, when the product was applied to TLC with elution by 1-butanol:glacial acetic acid:water (50:11:25). HPLC showed the endo/exo isomers as two peaks with retention times of 35.86 and 33.37 min, respectively (performed on a Brownlee Labs Spheri-5 RP 18 5 m column with a gradient elution at 1–13% CH$_3$CN in water, 0.2% per min). The ratio of the endo/exo isomers in an equilibrated aqueous solution is about 20:80.

Analysis (Found: C 28.78; H 3.33; I 45.8; N 5.12; Calc. for C$_{20}$H$_{28}$I$_3$N$_3$O$_9$; C 28.76; H 3.38; I 45.59; N 5.03).

RADIOLOGICAL COMPOSITIONS

N,N'-bis(1,3-dihydroxy-2-propyl)-5-[N-(2-hydroxy-3-methoxypropyl)acetamido]-2,4,6-triiodo isophthalamide (Compound A) of the present invention, trometamol (TRIS) and the edetate (CaNa$_2$ EDTA) are dissolved in water suitable for injection (approximately 950 ml). The pH is adjusted to 7.5 by means of hydrochloric acid 2M. and water suitable for injection is added to make the volume of the solution up to 1000 mls. The solution is membrane filered and dispensed into bottles or injection vials.

The infusion solutions are prepared in bottles of 250 ml and 500 ml, while solutions for injection are dispensed in 20, 50 and 100 ml injection vials.

The dispensed products are autoclaved for 20 mins at 120° C.

| Example | A | B | C | D | E | F |
|---|---|---|---|---|---|---|
| Compositions 1 liter | 100 mgI/ml Infusion | 150 mgI/ml Infusion | 180 mgI/ml Infusion | 240 mgI/ml Infusion | 350 mgI/ml Infusion | 440 mgI/ml Infusion |
| Compound I | 219 g | 329 g | 395 g | 526 g | 768 g | 965 g |
| Trometamol (TRIS) | 1.2 g | 1.2 g | 1.2 g | 1.2 g | 1.2 g | 1.2 g |
| Sodium-calcium-edtate (CaNa$_2$ EDTA) | 0.1 g | 0.1 g | 0.1 g | 0.1 g | 0.1 g | 0.1 g |
| Water for injection ad 1000 ml | | | | | | |
| HCl make pH 7.5 | 2M to | | | | | |

I claim:
1. A compound of the formula:

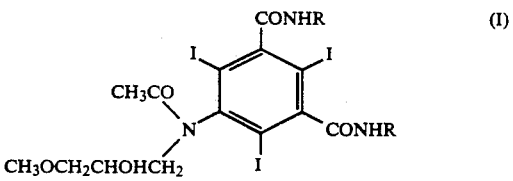

wherein R represents —CH(CH$_2$OH)$_2$ or —CH$_2$CH(OH)CH$_2$OH; including the stereoisomeric forms thereof separately or in combination.

2. N,N'-bis(1,3-dihydroxy-2-propyl)-5-[N-(2-hydroxy-3-methoxypropyl)acetamido]-2,4,6-triiodoisophthalamide.

3. N,N'-bis(2,3-dihydroxypropyl)-5-[N-2-hydroxy-3-methoxypropyl)acetamido]-2,4,6-triiodoisophthalamide.

4. A radiological composition comprising as active ingredient a compound of formula I as defined in claim 1 in association with an inert carrier.

5. A composition as claimed in claim 4 in vials or ampoules.

6. A composition as claimed in claim 5 wherein each vial or ampoule contains the said active ingredient in a concentration of from 20–500 milligrams I/ml.

7. An aqueous radiological composition comprising as active ingredient a non-ionic compound of claim 1.

8. A composition as claimed in claim 7 in vials or ampoules, wherein each vial or ampoule contains the said active ingredient in a concentration of from 20–500 mg I/ml.

* * * * *